(12) United States Patent
Resch

(10) Patent No.: US 8,355,137 B2
(45) Date of Patent: Jan. 15, 2013

(54) SYSTEM AND METHOD FOR CHIRPED PULSE INTERFEROMETRY

(76) Inventor: Kevin Resch, Waterloo (CA)

( * ) Notice: Subject to any disclaimer, the term of this patent is extended or adjusted under 35 U.S.C. 154(b) by 332 days.

(21) Appl. No.: 12/809,776

(22) PCT Filed: Dec. 19, 2008

(86) PCT No.: PCT/CA2008/002199
§ 371 (c)(1),
(2), (4) Date: Jun. 21, 2010

(87) PCT Pub. No.: WO2009/079759
PCT Pub. Date: Jul. 2, 2009

(65) Prior Publication Data
US 2010/0271635 A1 Oct. 28, 2010

Related U.S. Application Data

(60) Provisional application No. 61/008,593, filed on Dec. 21, 2007, provisional application No. 61/136,523, filed on Sep. 11, 2008.

(51) Int. Cl.
*G01B 9/02* (2006.01)
(52) U.S. Cl. .................................... 356/450
(58) Field of Classification Search .......... 356/450–452, 356/477
See application file for complete search history.

(56) References Cited

U.S. PATENT DOCUMENTS

| 5,479,256 A * | 12/1995 | Tamai et al. ............ 356/451 |
| 5,738,101 A * | 4/1998 | Sappey ............ 600/476 |
| 7,433,043 B2 * | 10/2008 | Birge et al. ............ 356/450 |
| 2006/0119855 A1 * | 6/2006 | Li ............ 356/450 |

FOREIGN PATENT DOCUMENTS

| WO | WO 98/01767 | 1/1998 |
| WO | WO 2006/053669 | 5/2006 |

OTHER PUBLICATIONS

M. Pessot, P. Maine, P. and G. Mourou, 1000 times expansion/compression of optical pulses for chirped pulse amplification. Opt. Commun. 62, 419 (1987).
A.M. Steinberg, P.G. Kwiat, and R.Y. Chiao, Dispersion cancellation in a measurement of the single photon propagation velocity in glass, Phys. Rev. Lett. 68, 2421 (1992).
J.D. Franson, Nonlocal cancellation of dispersion, Phys. Rev. A 45, 3126 (1992).

(Continued)

*Primary Examiner* — Michael A Lyons

(57) ABSTRACT

The device is based on a cross-correlator which measures the signal between a pair of oppositely chirped laser pulses. Two laser pulses, one with a positive chirp and one with a negative chirp, are mixed on a beamsplitter. The two resulting beams pass through a reference or a sample arm and are subsequently mixed on a non-linear crystal. The signal from the interferometer is the sum frequency generation produced in that crystal. The reference arm contains a moveable delay which is used to change the relative timing of the two beams in the interferometer. The sum frequency generation in the narrow band of frequencies is the signal from the device and is measured as a function of the delay. Alternatively, a pure dispersive phase shift could be used in place of the two laser pulses.

49 Claims, 14 Drawing Sheets

OTHER PUBLICATIONS

D.J. Kane and R. Trebino, Characterization of Arbitrary Femtosecond Pulses Using Frequency-Resolved Optical Gating, IEEE Journal of Quantum Electronics 29, 571 (1993).

A.B. Vankov, A.A. Chizhov, A.A. Kozlov, and V.E. Yashin, Chirped-pulse interferometry, CLEO Europe conference abstract (1996).

A. F. Fercher, W. Drexler, C. K. Hitzenberger, and T. Lasser, Optical coherence tomography—principles and applications, Rep. Prog. Phys. 66, 239 (2003).

Erkmen and J.H. Shapiro, Phase-conjugate optical coherence tomography, Physical Review A 74, 041601 (2006).

K. Banaszek, A. S. Radunsky, and I. A. Walmsley, Blind dispersion compensation for optical coherence tomography, Opt. Commun. 269, 152 (2007).

K.J. Resch, P. Puvanathasan, J.S. Lundeen, M.W. Mitchell, and K. Bizheva, Classical dispersion-cancellation interferometry, Optics Express 15, 8797 (2007).

R. Kaltenbaek, J. Lavoie, D. N. Biggerstaff, and K.J. Resch, Quantum-inspired interferometry with oppositely-chirped laser pulses, Nature Physics 4, 864 (2008).

J. Lavoie, R. Kaltenbaek, and K.J. Resch, 'Quantum-optical coherence tomography' with classical light, Optics Express 17, 3818 (2009).

R. Kaltenbaek, J. Lavoie, and K.J. Resch, Classical analogues of two-photon quantum interference, Physical Review Letters 102, 243601 (2009).

K.J. Resch, R. Kaltenbaek, J. Lavoie, D.N. Biggerstaff, Chirped-pulse interferometry with finite frequency correlations, Proceedings of SPIE 7465, 74650N (2009).

J. Le Gouët, D. Venkatraman, F.N.C. Wong, and J.H. Shapiro, Experimental realization of phase-conjugate optical coherence tomography, Optics Letters 35, 1001 (2010).

A. M. Steinberg et al, Dispersion cancellation and high-resolution time measurements in a fourth-order optical interferometer, Physical Review A, May 1, 1992, 6659-6665, 45:9.

James G. Fujimoto et al, Optical biopsy and imaging using optical coherence tomography, Nature Medicine, Sep. 1995, 970-972, 1:9.

C. Y. Chien et al, Single-shot chirped-pulse spectral interferometry used to measure the femtosecond ionization dynamics of air, Optics Letters, Apr. 15, 2000, 578-580, 25:8.

Ayman F. Abouraddy et al, Quantum-optical coherence tomography with dispersion cancellation, Physical Review A, May 8, 2002, 053817(1-6), 65.

Magued B. Nasr et al, Demonstration of Dispersion-Canceled Quantum-Optical Coherence Tomography, Physical Review Letters, Aug. 22, 2003, 083601(1-4), 91:8.

Magued B. Nasr et al, Dispersion-cancelled and dispersion-sensitive quantum optical coherence tomography, Optics Express, Apr. 5, 2004, 1353-1362, 12:7.

Avi Pe'er et al, Broadband sum-frequency generation as an efficient two-photon detector for optical tomography, Optics Express, Jul. 9, 2007, 8760-8769, 15:14.

Cristian Bonato et al, Even-Order Aberration Cancellation in Quantum Interferometry, Physical Review Letters, Dec. 5, 2008, 233603 (1-4), 102.

Olga Minaeva et al, Odd- and Even-Order Dispersion Cancellation in Quantum Interferometry, Physical Review Letters, Mar. 13, 2009, 100504 (1-4),102.

Magued B. Nasr et al, Quantum optical coherence tomography of a biological sample, Optics Communications, 2009, 1154-1159, 282.

* cited by examiner

PRIOR ART

SYSTEM AND METHOD FOR CHIRPED PULSE INTERFEROMETRY

PRIORITY

This application claims priority to U.S. provisional patent application No. 61/008,593 filed Dec. 21, 2007 and U.S. provisional patent application No. 61/136,523 filed Sep. 12, 2008.

FIELD OF THE INVENTION

The present invention relates generally to optical interference. The present invention relates more specifically to an analogue of the Hong-Ou-Mandel interferometer that by using laser light instead of entangled photons is operable to provide a substantial improvement thereupon.

BACKGROUND TO THE INVENTION

Interference is a defining feature of both quantum and classical theories of light enabling precise measurements of a wide range of physical quantities including length and time. Quantum metrology exploits fundamental differences between these theories for new measurement techniques and enhanced precision. Advantages stem from several phenomena associated with quantum interferometers, including non-local interference, phase-insensitive interference, phase super-resolution and super-sensitivity, and automatic dispersion cancellation.

Arguably, the best known example of quantum interference was demonstrated by Hong, Ou, and Mandel ("HOM"). FIG. 1 illustrates a HOM interferometer in accordance with the prior art. HOM interference is now considered central to optical quantum technologies, including quantum teleportation and linear-optical quantum computing. Several characteristics distinguish HOM from classical interference, such as Michelson's or Young's. The HOM signal stems from pairs of interfering photons and manifests as a dip in the rate of coincident photon detections spanning the coherence length of the light, as opposed to classical wavelength fringes. It is therefore inherently robust against path length fluctuations. If the photons are entangled, the visibility and width of the HOM interferogram is typically insensitive to loss and dispersion. Furthermore, HOM interferometers typically achieve higher resolution than classical interferometers using the same bandwidth. These features are ideal for precision optical path measurements of dispersive and lossy materials, implemented by placing the sample in one interferometer arm and measuring the delay required to restore interference. Unfortunately, quantum interferometers require entangled states that are practically difficult to create, manipulate, and detect, especially compared with robust, intense classical states.

Optical coherence tomography (OCT) is a non-invasive imaging technique using low-coherence interferometry to produce depth profiles of a sample. OCT has found many biomedical applications including diagnosis of ocular diseases or detection of early-stage cancer. Axial resolution in OCT is typically ultimately limited by the coherence length of the light source and can be less than 1 μm for very broadband sources. This resolution is typically hindered by material dispersion which serves to both broaden features in the interferograms and reduce contrast. A quantum version of optical coherence tomography (QOCT) has been shown to harness the advantages of HOM interference. QOCT combines the idea of HOM interference with a standard time-domain OCT system to harness the advantages of HOM interference. QOCT techniques have not found widespread application because they suffer from the difficulties of working with entangled photons, such as expensive, complex experimental setups and low signal levels. QOCT, which replaces white light interference (WLI) with a HOM interferometer based on frequency-entangled photon pairs, automatically cancels all even orders of dispersion (including the most significant, group-velocity dispersion) in the resulting interferogram, allows for dispersion cancellation to be "blind" (i.e. requiring no a priori knowledge of the material properties), is phase insensitive, has better resolution than WLI with the same bandwidth, and provides an interference visibility that is insensitive to unbalanced loss. Unfortunately, the HOM interferometer utilized in QOCT is based on entangled photon pairs and the costs, in terms of speed, and specialized & expensive equipment, have limited its widespread adoption. Other techniques for blind dispersion compensation without entanglement have been proposed or demonstrated, but they require unavailable technology or significant numerical post-processing and do not have the other properties of HOM interference.

There are several other techniques which have been used to cancel dispersion in WLI/OCT which each fail to provide a fully beneficial result, including compensating dispersion (which only approximates cancellation and even then is useful only for dispersion cancellation at certain depths of the sample), numerical algorithms (which require a priori knowledge of characteristics of the sample), use of broadband modulators and multipass interferometry (which are very difficult to implement), use of physical assumptions about the material (which also require a priori knowledge of characteristics of the sample), and white-light spectral interference in conjunction with computing a correlation function (which require a large amount of data to be taken and a substantial numerical post-processing). Other techniques require wavelength path stability such that the interference visibility falls precipitously with loss and is limited to 50% of that possible with the HOM effect. Alternatively, background-free autocorrelation of transform-limited pulses, recently used for OCT, exhibits enhanced resolution, phase insensitivity, and robustness against loss, but notably not automatic dispersion cancellation. Other phase-insensitive classical interferometers achieve their phase insensitivity by ensuring that the interfering paths travel through common optics, or even common spatial paths. They are therefore incapable of measuring delays through interference since the relative path lengths cannot be changed.

Therefore, what is needed is an interferometer that does not require entangled photons yet achieves all of the benefits of an HOM interferometer, including: phase-insensitive interference, high interference contrast, automatic dispersion cancellation, and insensitivity to loss. What is also needed is such an interferometer that can achieve these features without requiring a priori knowledge of the nature of the material or extensive numerical post-processing of data.

SUMMARY

In one aspect of the present invention, an interferometer system for measuring optical properties of a sample is provided, the interferometer system characterised by: (a) a light source apparatus operable to emit at least one shaped laser pulse toward a beam splitting apparatus; (b) the beam splitting apparatus operable to (i) mix the at least one shaped laser pulses so as to define a mixed beam; and (ii) separate the mixed beam so as to define two resulting beams, a first resulting beam directed to a reference arm and a second resulting beam directed to a sample arm, the sample being associated with the sample arm; (c) a combining apparatus operable to receive the two resulting beams after the two resulting beams exit the reference arm and the sample arm, the combining apparatus combining the two resulting beams into a product beam, the combining apparatus further directing the product beam towards a detection point; and (d) a detector operable to record at the detection point an interference pattern for defining the optical properties, the interference pattern corresponding to the product beam.

In another aspect of the present invention, an interferometric method for measuring optical properties of a sample is provided, the interferometric method characterised by: (a) generating at least one shaped laser pulse; (b) mixing the at least one shaped laser pulse so as to define a mixed beam; (c) separating the mixed beam so as to define two resulting beams, a first resulting beam directed to a reference path and a second resulting beam directed to a sample path, the sample associated with the sample path; and (d) combining the two resulting beams after the two resulting beams exit the reference path and the sample path into a product beam, the product beam corresponding to an interference pattern for defining the optical properties.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION

Overview

The present invention provides an analogue to a HOM interferometer that advantageously uses only laser light in the form of shaped laser pulses, which may be in the form of oppositely chirped optical pulses to overcome the challenges inherent in the use of photon entangled interferometers. The present invention is operable to provide signal intensities multiple orders of magnitude greater than that achievable using photon entangled interferometers.

The present invention, in one aspect thereof, provides an interferometer producing an interference signal that is the same shape as that produced by the HOM interferometer, thus achieving its array of metrological advantages, including phase insensitivity, increased resolution, dispersion cancellation, and insensitivity to loss. The entangled photon limitation of the HOM interferometer may be overcome using intense classical beams that advantageously produce a correspondingly high signal. An implementation disclosed herein is operable to provide a ten-million-fold increase in signal over a state-of-the-art quantum implementation.

The present invention further achieves phase insensitivity because the interfering Feynman paths share common spatial paths. However, unlike standard classical interferometers, the Feynman paths do not directly represent a single physical path, but rather pairs of paths taken by light with different frequencies. This provides phase insensitivity but also allows sensitivity to optical delays, which may be required for measurement of these physical quantities.

The technique disclosed is a blind dispersion cancellation, meaning that no assumptions need be required about the nature of the material. Furthermore, manual dispersion compensation between the two interferometer arms is not required. The sum frequency signal output by the device may be automatically dispersion compensated. This is considerably simpler than computing a function on the entire data set or nonlinear curve fitting.

Figure 2:
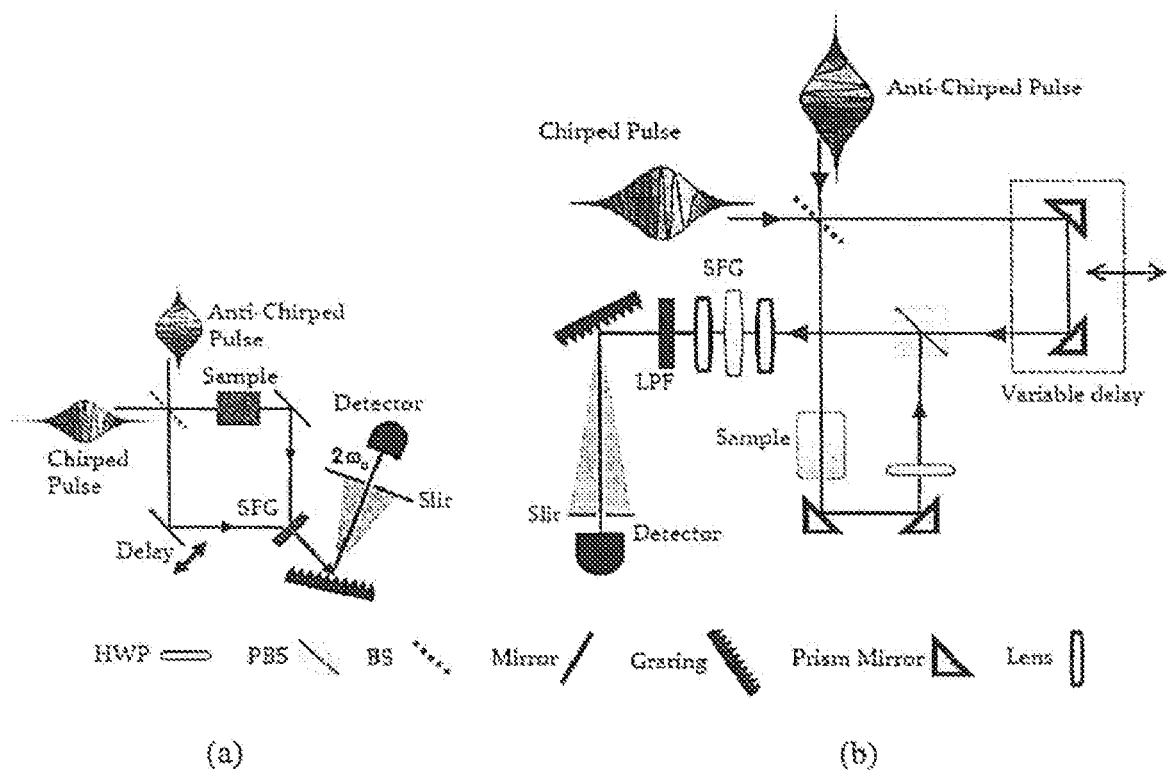
FIG. 2 illustrates the CPI interferometer in accordance with the present invention, in one aspect thereof, and an example implementation thereof.

FIG. 2 illustrates a chirped pulse interferometer in accordance with the present invention, in one aspect thereof, and an example implementation thereof. FIG. 2*a* illustrates the system of the present invention, in one aspect thereof, which is hereinafter referred to as a chirped pulse interferometer (the "CPI"). The CPI, in one aspect thereof, may be based on a cross-correlator which measures the signal between a pair of shaped laser pulses. The shaped laser pulses, in one aspect of the present invention, may be any shaped laser pulses that create a time correlation between anticorrelated frequencies. More particularly, the shaped laser pulses may be oppositely-chirped laser pulses comprised of two laser pulses, one with a positive chirp and one with a negative chirp. The oppositely chirped laser pulses could also be provided by two different synchronized lasers, wherein one produces chirped pulses and the other produces antichirped pulses. In another aspect of the present invention, a pure dispersive phase shift may be used to enable the CPI to be operable with just one input optical beam rather than two.

The shaped laser pulses may be mixed on a beamsplitter. The two resulting beams may pass through a reference or a sample arm and may be subsequently mixed on a nonlinear material, such as a crystal. The signal from the interferometer may be the sum-frequency generation (SFG) produced in the crystal. The length of the reference arm may be moved to adjust the delay of the beam which may be used to change the relative timing of the two beams in the interferometer. The sum-frequency generation in a narrow band of frequencies may be the signal from the device and may be measured as a function of the delay.

The CPI may produce a signal somewhat similar to that in white light interferometry in that the SFG displays interference over a short range of delay positions. The resolution of the device may be increased by increasing the bandwidth of the chirped pulses. Like white-light interference, the delay required to achieve interference may be dependent on the group delay between the two arms including the group delay of a sample.

The interference produced by the device may have several characteristics distinguishing it from white light interference, including phase-insensitivity over the coherence length of the light instead of the wavelength and therefore inherent insensitivity to path length fluctuations, the shape and visibility of the chirped-pulse interference pattern being completely insensitive to loss and even-order dispersive broadening, and the chirped-pulse interference pattern having intrinsically higher resolution than the white-light interference.

Hong-Ou-Mandel-Based Metrology

In order to best understand the present invention, it may be beneficial to describe briefly the HOM metrology model. In HOM metrology, the wavevector of light in a material may be expanded about a frequency $\omega_0$, $k(\omega)=k(\omega_0)+\alpha(\omega-\omega_0)+\beta(\omega-\omega_0)^2+\ldots$, where $\alpha$ and $\beta$ are material properties describing the group delay and quadratic group velocity dispersion (GVD) of the material, respectively.

Ideal frequency-entangled photon pairs may be described by the state, $|\psi\rangle = \int d\Omega f(\Omega)|\omega_0+\Omega\rangle|\omega_0-\Omega\rangle$, where $f(\Omega)$ is the amplitude spectrum. The coincidence rate in the HOM interferometer as a function of the relative delay time, $\tau$, may be given by, $$C(\tau) = \int d\Omega |f(\Omega)|^2 \{1-\cos[\phi_{rr}(\Omega,\tau)-\phi_{tt}(\Omega,\tau)]\} \quad (1)$$

where $\phi_{rr}(\Omega,\tau)(\phi_{tt}(\Omega,\tau))$ are the phases associated with the amplitude where both photons are reflected (transmitted); the delay time $\tau=(L_2-L_1+L)/c$, where $L_1$ ($L_2$) is the length of the sample (delay) arm and L is the length of the sample; and $\phi_{rr}(\Omega,\tau)=L(+\alpha\Omega+\beta\Omega^2)-\Omega\tau$ and $\phi_{tt}(\Omega,\tau)=L(-\alpha\Omega+\beta\Omega^2)+\Omega\tau$, after removing an irrelevant global phase.

Since $\phi_{rr}(\Omega,\tau)$ and $\phi_{tt}(\Omega,\tau)$ may have the same dependence on the GVD, $\beta$, they may automatically cancel in the interference signal, as may all even orders of dispersion. The coincidence rate may drop to zero for $\tau=\alpha L$ (when the group delay from the material is exactly compensated by unequal physical path lengths). This may mark the centre of the HOM dip.

Mathematical Basis of the Present Invention

Figure 1:
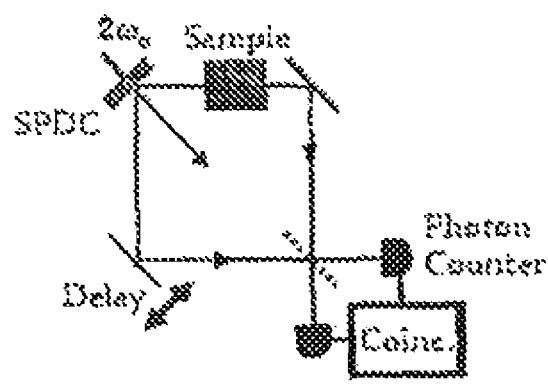
FIG. 1 illustrates a typical HOM interferometer in accordance with the prior art.

The present invention may be understood with reference to the cross-correlator shown in FIG. 2a as a time-reversed HOM interferometer illustrated in FIG. 1. The detection of a pair of photons with frequencies $\omega_0\pm\Omega$ may be replaced by the preparation of a pair of photons with those frequencies; the preparation of a pump photon of frequency $2\omega_0$, which is subsequently down-converted, may be replaced by the detection of a photon of frequency $2\omega_0$, which had previously been up-converted. Thus the signal given above in Eq. 1 may be built up by repeating the process using pairs of photons with frequencies distributed according to the spectrum, $|f(\Omega)|^2$.

The novelty of the present invention, in one aspect thereof, stems from the replacement of photon pairs by bright classical beams, such as laser light beams, with frequencies $\omega_0\pm\Omega$. The SFG from these beams may contain three distinct frequencies, instead of just one: the cross-correlation may produce up-converted light at $2\omega_0$ at a rate proportional to $\{1-\cos[\phi_{rr}(\Omega,\tau)-\phi_{tt}(\Omega,\tau)]\}$ (cf. Eq. 1); the autocorrelation may produce two new beams at frequencies $2\omega_0\pm2\Omega$. A narrow bandpass filter centred at $2\omega_0$ may remove the autocorrelation unless $\Omega$ is small.

The frequency difference, $\Omega$, may be swept using pairs of shaped laser pulses that are time correlated and frequency anticorrelated. A shaped laser pulse may have an optical frequency that may ramp linearly in time, and may optimally be chirped and anti-chirped laser pulses. The chirp and anti-chirp may optimally be much greater than any dispersion in the interferometer and stretch the pulses to many times their initial duration. By using pairs of oppositely-chirped pulses that have been stretched several hundred times their initial, transform-limited pulse duration, one can consider the CPI just two frequencies at a time, $\omega_0+\Omega$ and $\omega_0-\Omega$; if the chirped pulses are coincident at the input beamsplitter, the $\omega_0$ may be equal to the centre frequency of the laser, and it can be tuned by changing the relative delay between the pulses. The ramp may perform the integration in Eq. 1 automatically. As an added benefit, chirped pulses may have high peak intensities yielding efficient frequency conversion.

Example Implementation

FIG. 2b illustrates the interferometer system of the present invention, in one aspect thereof. Beams of chirped and anti-chirped laser pulses may be created from a modelocked laser and injected into the system of the present invention. The relevant centre frequency may not be the centre frequency of the pulse, but rather may be determined by the temporal overlap of the chirped and anti-chirped pulse at a beamsplitter. If the chirped pulse lags (or leads) the anti-chirped pulse, the frequency $2\omega_0$ may be red-shifted (reduced) or blue-shifted (increased) from twice the centre frequency of the laser. This may be used to make measurements of group delays over a tunable range of wavelengths, which is difficult to do using HOM interference where the entangled photons are typically produced using a fixed frequency CW laser.

The modelocked laser may be, in one particular example implementation of the present invention, a modelocked ti:sapphire laser characterised by a centre wavelength of 790 nm, pulse duration of 110 fs, average power of 2.8 W, and repetition rate of 80 MHz. The polarization of the output may be rotated from vertical to horizontal using a half-wave plate to achieve maximum diffraction efficiency from our gratings. A 50/50 beamsplitter may be provided for splitting the laser light. Half of the optical power may be sent through a grating-based optical compressor and the other half may be sent through a grating-based optical stretcher. The stretcher may apply normal dispersion, creating a chirped pulse where the blue lags the red in time, whereas the compressor may apply anomalous dispersion, creating an anti-chirped pulse where the red lags the blue. While the terms stretcher and compressor are commonly used, in the aspect herein described both devices stretch the optical pulses. Both the stretcher and compressor may be characterised by 30 mm×30 mm, 1200 lines/mm gold-coated ruled diffraction gratings, blazed for 800 nm.

In the compressor, the gratings may be oriented with their faces parallel and separated by a distance of 56 cm. The input beam may pass over the top of a prism mirror, and the retro-reflecting mirror may be angled slightly downward so that the output beam is reflected by the prism mirror. The compressor may produce anti-chirped output pulses 45.1±0.1 ps long with 9 nm of bandwidth and the beam having an average power of 790 mW.

In the stretcher, the gratings may be oriented with their faces antiparallel and separated by a distance of 145 cm. A 1:1 telescope may be placed between the gratings, consisting of two lenses f≈50 cm separated by 98.5 cm with the first lens placed 9.2 cm after the first grating. The stretcher may produce chirped output pulses 51.2±0.2 ps long with 10 nm of bandwidth and the beam may have an average power of 870 mW.

The stretcher and compressor may be balanced by sending the output of the stretcher through the compressor and minimizing the pulse duration of the output by changing the grating separation in the compressor. A broadening of approximately 10% may be observed versus pulses directly from the laser. The differences between the durations of the chirped and anti-chirped pulses may be due to unequal loss of bandwidth in the stretcher and compressor. They may not reflect different chirp rates.

The chirped and anti-chirped pulses may be spatially and temporally overlapped at the input broadband beamsplitter cube of the cross-correlator previously illustrated in FIG. 2a. To compensate for the shorter optical path in the compressor as compared to the stretcher, the anti-chirped pulse may arrive at the beamsplitter via a variable delay path (not illustrated in FIG. 2a). The delay may be set such that the sum of the frequencies of the chirped and anti-chirped pulses at any given time correspond to a wavelength of 395.9 nm. Note that this need not equate to exactly half the centre wavelength of the laser and can be continuously tuned by varying the time-delay between chirped and anti-chirped input beams.

The two outputs from the beamsplitter may travel different paths through the cross-correlator. One may travel through the delay arm where a retro-reflector may be placed on a motorized translation stage with 40 mm travel; the other may pass through the sample and an achromatic half-wave plate which rotates the polarization from horizontal to vertical. The two beams may be recombined at a broadband polarizing beamsplitter cube (PBS).

The output from the PBS may be focused by a 5-cm achromatic lens into a 0.5-mm β-barium-borate (BBO) optical crystal cut for collinear type-II degenerate SFG. The sum-frequency beam may then be collimated by means of another 5-cm lens. The infrared light may be filtered by means of two dichroic mirrors (not shown) designed to reflect 395-nm light at 45° incidence and to transmit 790-nm light, as well as a cyan coloured glass low-pass filter; this is depicted as a low-pass filter (LPF) in FIG. 2b. A 0.4 nm band of light centred at 395.9 nm may be filtered using a 1200 lines/mm aluminum-coated diffraction grating followed by a slit. The optical power may be measured using an amplified silicon photodiode. In such an aspect, a photodiode may register a bias ranging from −30 mV to −40 mV when in the dark. This may be an important measure to calibrate the measured voltage of the system. This bias correction may lower reported visibilities.

The system of the present invention, in accordance with the aspect herein described, may be operable where the pulses are combined such that the sum of the frequencies corresponds to a wavelength, 395.9 nm, well separated from half of the centre wavelength of a laser, 395.0 nm, as previously described.

Figure 3:
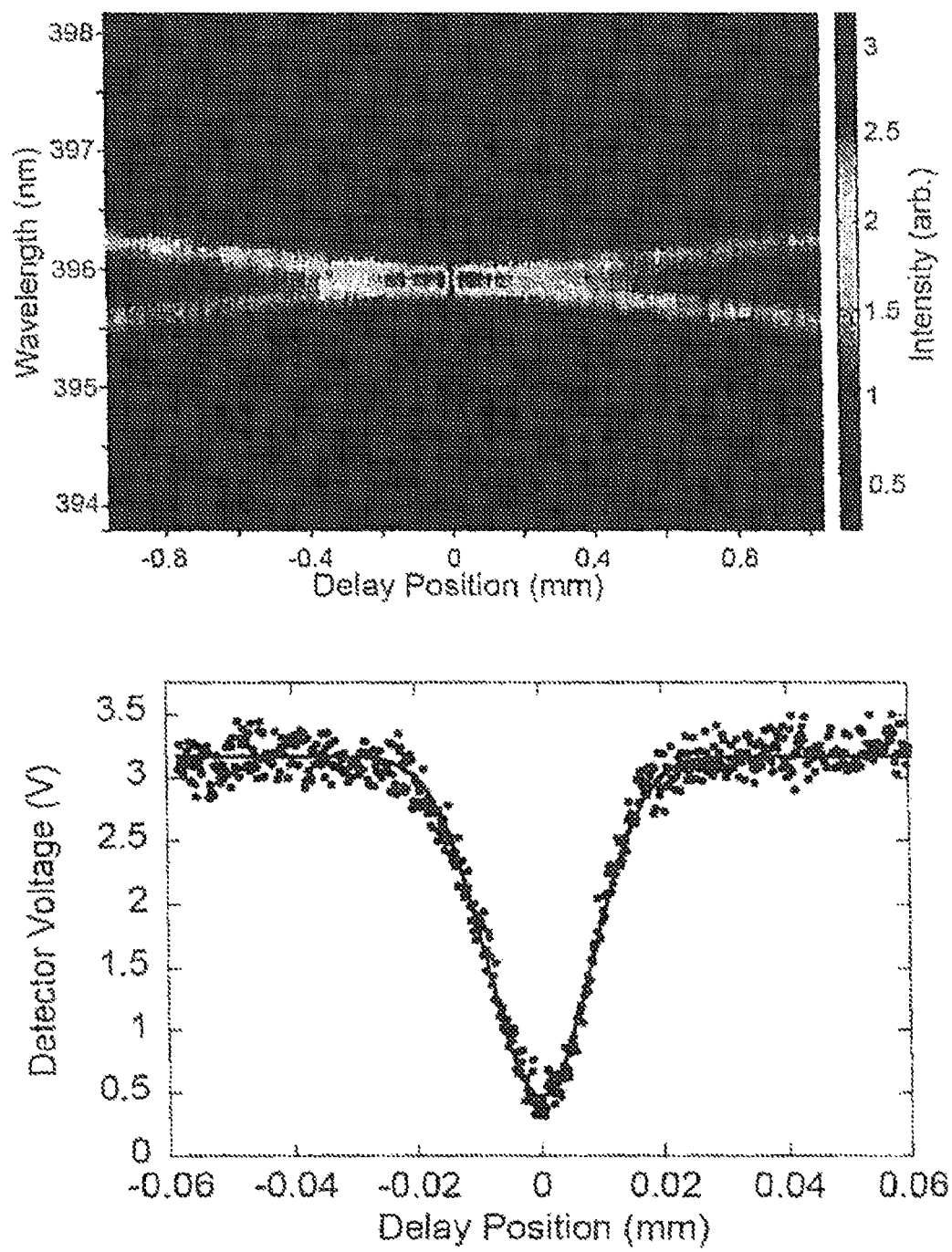
FIG. 3 illustrates measured SFG spectrum and photodiode signal versus delay for an example implementation of the system of the present invention, in one aspect thereof.

FIG. 3 illustrates measured SFG spectrum and photodiode signal versus delay for an example implementation of the system of the present invention, in one aspect thereof. The cross-correlation signal may be clearly observed in FIG. 3a, but the autocorrelation signal may comprise a broad background barely visible on this scale. For large delays, the cross-correlation may contain two easily-discernable wavelengths spaced symmetrically about 395.9 nm. These peaks may arise from SFG of the chirped component in the sample arm and the anti-chirped component in the delay arm, and vice versa. These different alternatives may constitute the distributed Feynman paths, which may interfere. The two wavelengths may approach one another as the path length difference approaches zero, where destructive interference may eliminate the cross-correlation signal.

The bandwidth of 0.4 nm centred at 395.9 nm may be filtered and the intensity may be measured with an amplified silicon photodiode. FIG. 3b illustrates the photodiode signal as a function of delay, which clearly shows the interference dip with visibility 85.2±0.6% and FWHM (Full Width at Half Maximum) 19.9±0.6 µm or 133±1 fs. The signal-to-noise ratio of the system of the present invention, in one aspect thereof, may be limited by interference of the beams at the input beamsplitter; this noise source can be removed by path-length stabilization or by blocking a narrow band of frequencies near $\omega_0$.

The system of the present invention, in one aspect thereof, may be capable of surpassing the 50% limit commonly attributed to classical analogues of HOM interference. This classical limit applies only to the visibility of the coincidence rate (or correlation) between two square-law photodetector signals showing no individual interference. Although both SFG and coincidence detection measure correlations, the SFG signal depends on the product of the electric fields, as opposed to intensities. The system of the present invention avoids this constraint.

Moreover, with the system of the present invention, in one aspect thereof, background from the autocorrelation may limit the visibility, but visibility could be arbitrarily close to 100% with large chirp and narrow filtering. Alternatively, one could achieve 100% visibility by removing the small band of frequencies responsible for the autocorrelation background from the chirped and anti-chirped pulses; however, this may produce the drawback of distorting the interferogram.

In the implementation herein described, the optical power corresponding to 1V may be measured at approximately 1.5 µW at 395 nm. With the parameters described above, a measured signal of 4.5 µW may be achieved, corresponding to about $10^{13}$ photons/s. A coincidence rate from a photon pair source may reach $2 \times 10^6$ Hz, which corresponds to a measure several orders of magnitude higher than in a HOM interferometer. Certain state of the art photon pair sources may achieve a 7-order-of-magnitude increase in signal over a HOM interferometer in accordance with the implementation herein described.

Demonstration of the Benefits of the Present Invention

Figure 4:
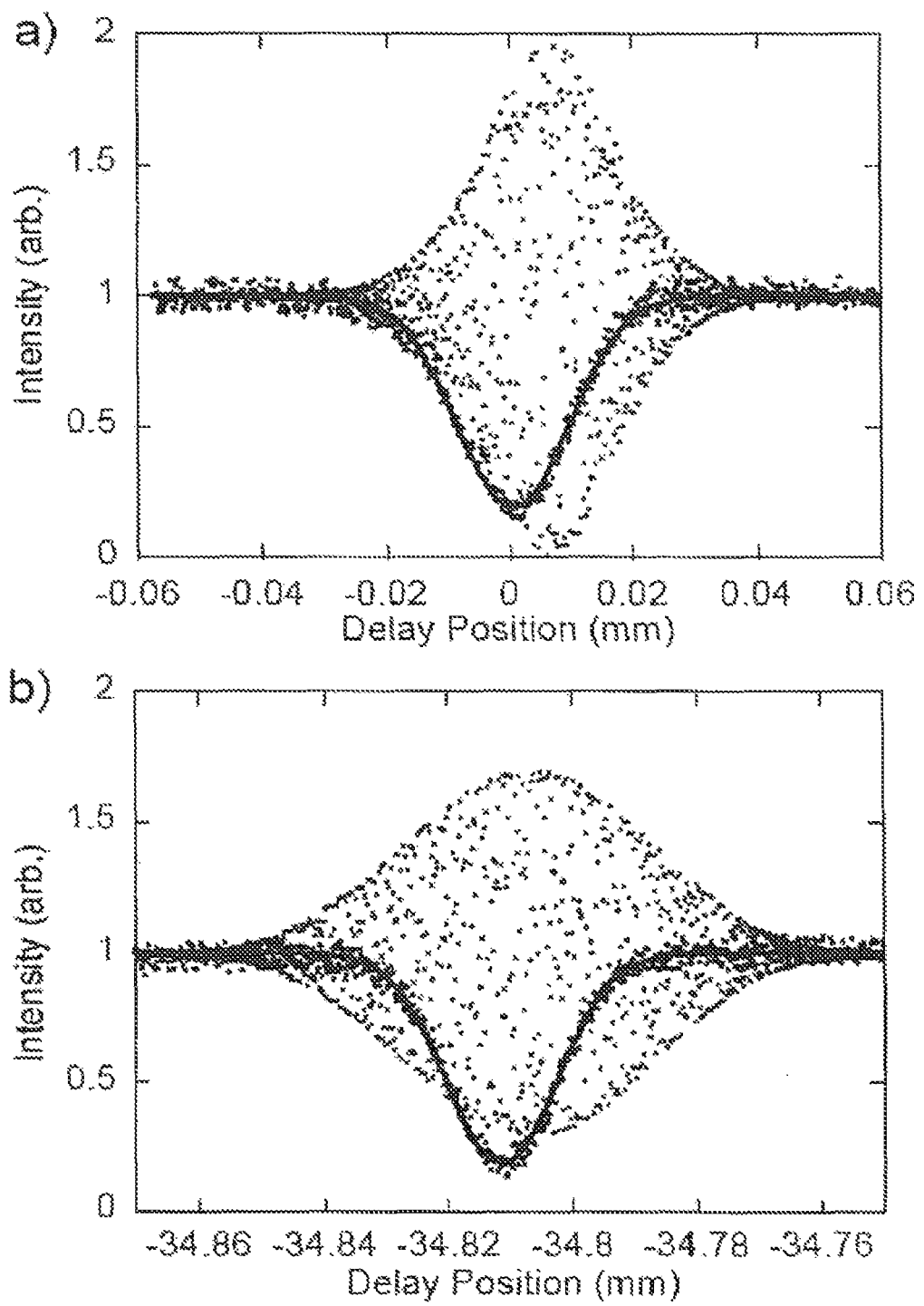
FIG. 4 illustrates resulting interferograms of the present invention, in one aspect thereof, demonstrating automatic dispersion cancellation using the example implementation herein described.

FIG. 4 illustrates resulting interferograms of the present invention, in one aspect thereof, demonstrating automatic dispersion cancellation using the example implementation herein described wherein two data sets may be utilized: one with significant dispersive material in the sample arm, such as 80.60±0.05 mm of calcite and 28.93±0.04 mm of BK7 glass, and one without. In each configuration chirped-pulse and white-light interferograms may be measured. By sending a chirped pulse through the interferometer with a polarizer placed at 45° before the nonlinear crystal, the white-light interference may be directly detected using the transmitted infra-red light.

FIG. 4a illustrates an interferogram corresponding to the sample arm not being populated by a sample. With no sample, 143±2 fs FWHM is observed for the chirped-pulse dip and 173±1 fs FWHM is observed for the white-light interference pattern; the chirped-pulse signal has 17% better resolution. The system of the present invention can be shown to have at least 29% better resolution than a typical HOM interferometer by integrating Eq. (1) with Gaussian spectra for both the chirped and anti-chirped pulses, i.e., $|f(\Omega)|^2 = G(\Omega)G(\Omega)$, and comparing that to white-light interference with the spectrum, $G(\Omega)$). The difference between theory and values measured in practice may be attributed mainly to lost bandwidth in SFG.

FIG. 4b illustrates an interferogram corresponding to the insertion of dispersive elements in the sample arm. With the dispersive elements, 140±2 fs FWHM may be observed for chirped-pulse interference and 303±2 fs FWHM is observed for white-light interference. Dispersion may increase the width of the white-light interference pattern by 75%; the width of the pattern produced by the present invention may remain essentially unchanged due to dispersion cancellation.

To show that the present invention accurately determines group delays, shifts in the centre of the interference may be measured at approximately 34811.9±0.3 μm and 34813.80±0.3 μm for the chirped-pulse dip and white-light fringes, respectively. These agree with theoretical shifts of 34816±20 μm and 34822±20 μm, calculated from the group delays at 791.8 nm and 790 nm, respectively.

Any mathematical uncertainties specified above may be attributed to errors in the measurement of sample thickness.

Figure 5:
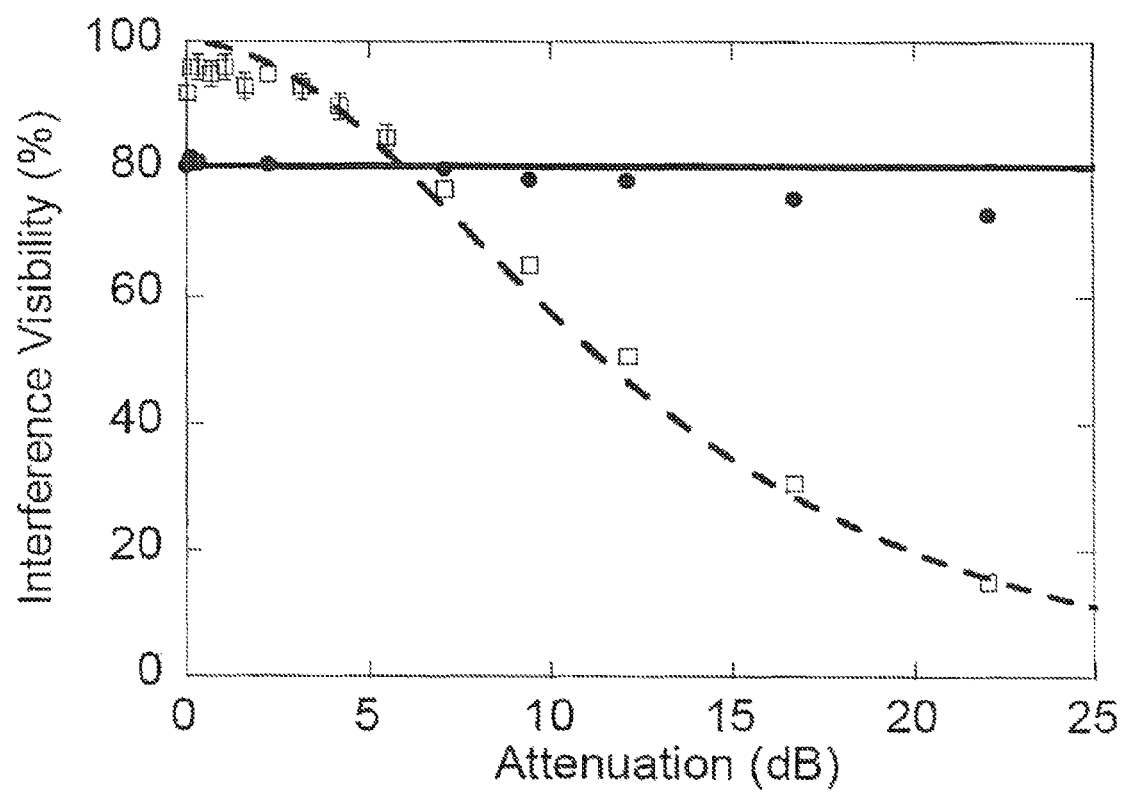
FIG. 5 illustrates visibilities as a function of attenuation in accordance with the present invention, in one aspect thereof.

FIG. 5 illustrates visibilities as a function of attenuation in accordance with the present invention, in one aspect thereof. A further advantage of the present invention over white-light interferometry is the insensitivity of the visibility (i.e. the signal contrast) to unbalanced loss in the interferometer arms; loss may, however, reduce the overall output intensity, and therefore the signal, in both cases. This insensitivity may be explained by noting that, in the present invention, the loss is common to both interfering Feynman paths even though it is localized in one physical path. This advantage may enable a reduction in the required output power of the laser used in the present invention, which has several advantages. The visibilities, as a function of attenuation, may be measured for the present invention. Rotating a half-wave plate in the sample path may enable continuous adjustment of the loss at the polarizing beam splitter.

The system and method of the present invention therefore provably feature all of the metrological advantages of HOM interference with vastly higher signal levels, and achieve this without the inherent disadvantages of entangled photon sources and single-photon detection. By increasing the laser bandwidth and the spectral acceptance of SFG, the present invention may be characterised by resolution competitive with that in OCT. The present invention is especially advantageous for measurement of dispersive and lossy media, such as biological specimens and photonic devices, due to automatic dispersion cancellation and insensitivity to loss and path length fluctuations. This approach also provides an avenue into previously untapped potential of classical interferometry.

CPI Analogues to 2-Photon Interference Quantum Effects

As is known to those skilled in the art, certain modifications to a typical HOM interferometer can produce qualitatively different interference effects.

It can be shown that by introducing similar changes to the CPI of the present invention, similar effects can be produced. For example, modifications to the CPI can produce a result wherein the sign of the interference changes from destructive (i.e. dips) to constructive (i.e. peaks). It is also possible to control the wavelength of the interference pattern to achieve either interference with a much longer or shorter period than the wavelength of light. Therefore, the CPI could be used to achieve with purely classical means each of the three very distinct interferograms known to be achievable using modifications to the HOM interferometer. The three effects include the Hong-Ou-Mandel peak, quantum beating, and phase super-resolution.

Figure 6:
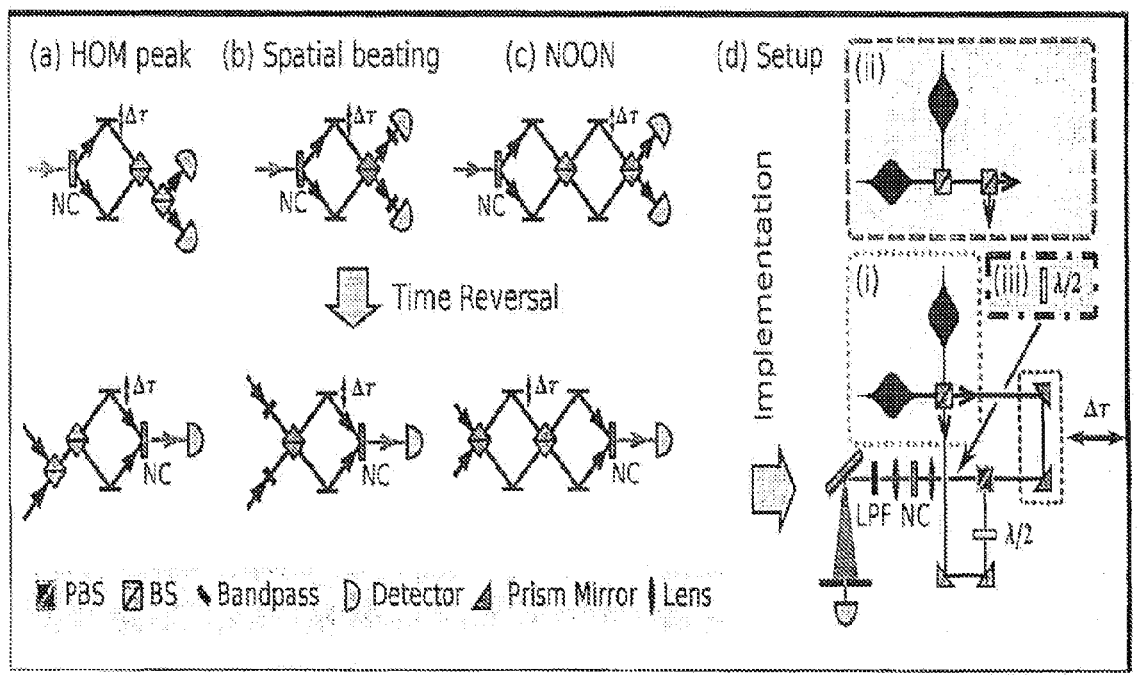
FIG. 6 illustrates the CPI of the present invention, in one aspect thereof, providing three quantum-interferometric schemes achievable using entangled photon interferometers.

FIG. 6 illustrates that the CPI, implemented as described above, can be modified to produce the same signal as three different quantum-interferometric schemes achievable using entangled photon interferometers. As previously mentioned, the CPI may be based on a time-reversed HOM interferometer. Correspondingly, it can be shown that modifications to the CPI that correspond exactly to the modifications made to the HOM interferometer produce CPI signals that exactly mimic the quantum interference effects known as the HOM peak, quantum beating, and phase super-resolution.

The HOM peak is the opposite of the HOM dip. In order to observe this peak HOM interferometers are typically modified by placing a second beam splitter in one of the output modes of the first beam splitter, as illustrated in FIG. 6a.

Figure 7:
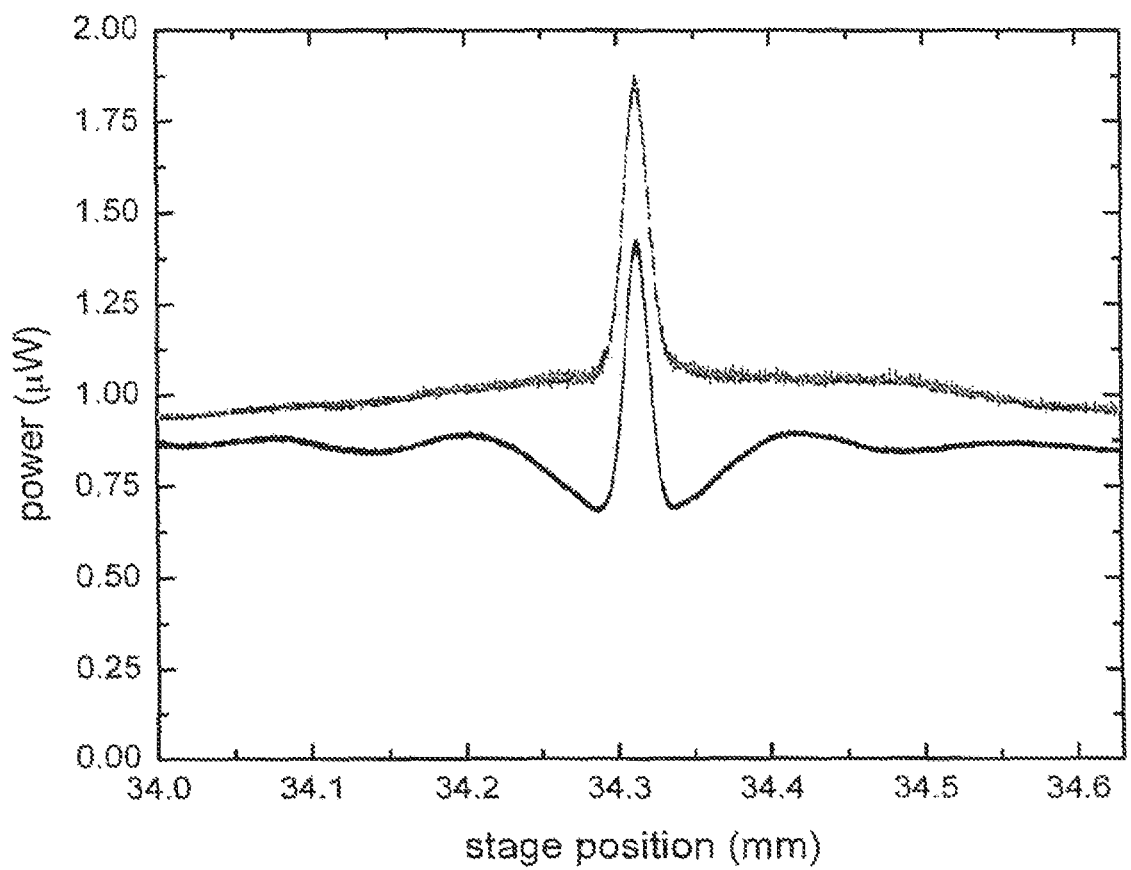
FIG. 7 illustrates the result of a scan wherein the oppositely chirped beams of the CPI are overlapped before injection into an autocorrelator.

Time-reversing the HOM-peak setup, illustrated in FIG. 6a, may be achieved by overlapping the oppositely chirped beams on a beam splitter before injecting them into the autocorrelator (see FIG. 6d). FIG. 7 illustrates the result of a scan in this configuration, the upper curve of which shows a distinct peak in full analogy to a HOM interferometer with a visibility of ~70%. Blocking part of the spectrum around $\omega_0$ in front of one of the single-photon detectors may lead to a reduced coincidence rate close to the HOM peak. An analogous effect may be observed quantum mechanically and attributed to enhanced photon pair absorption due to exchange effects. The present invention is operable to achieve an analogous signal if part of the spectrum of one of the input beams is blocked around $\omega_0$ by blocking part of the beam in the grating-based stretcher. The lower curve illustrated in FIG. 7 shows the result. Like in the quantum case a distinct drop of the signal may be observed close to the peak.

Optimally, both scans may be observed by changing the path delay in the delay arm of the autocorrelator with a constant velocity of 0.5 mm/s. Simultaneously, data may be taken with a sample rate of 12 kHz. The grating and the slit to filter the SFG signal may be adjusted to filter a bandwidth of 0.4 nm FWHM around the center wavelength 395.1 nm.

Quantum beating can typically be observed in a HOM interferometer if a pair of interference filters with different bandpasses (i.e. with a difference in central wavelengths comparable to or larger than the filter bandwidths) is placed in front of the detectors (see FIG. 6b).

To realize the time-reversal of HOM interference with quantum beating, parts of the spectra of the chirped and anti-chirped beam may need to be blocked. To achieve optimal SFG efficiency, the sum of the center-frequencies of the filtered chirped and anti-chirped beams should be $2\omega_0$. This can be achieved by blocking part of the spectrum in the stretcher and the compressor.

Figure 8:
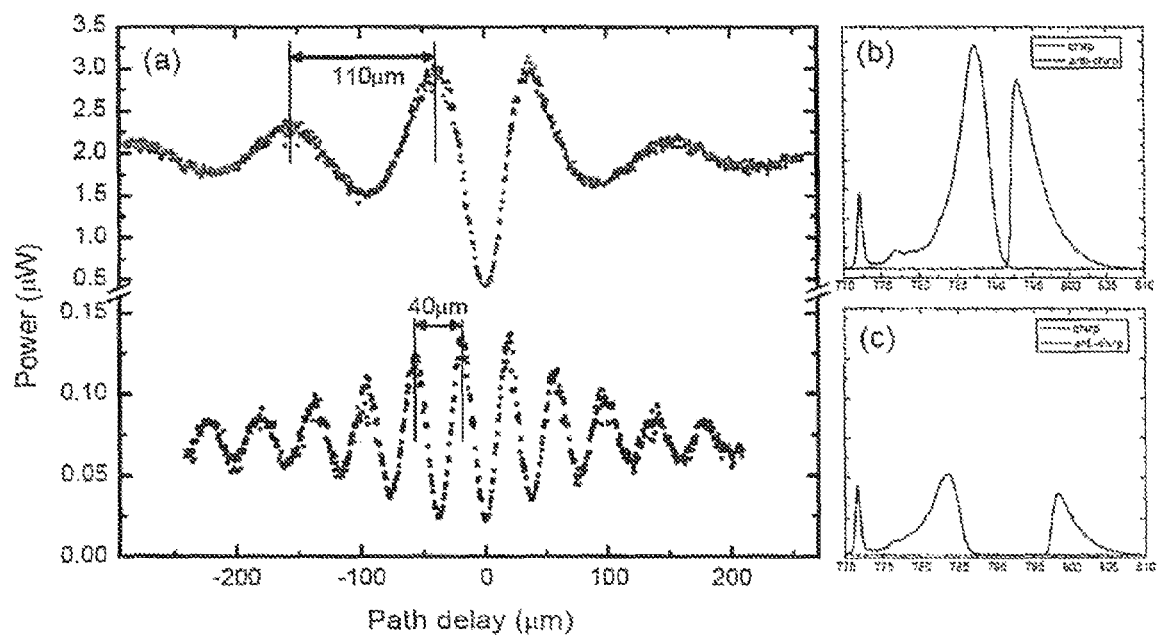
FIG. 8 illustrates representative scans and filtered spectra for two alternate configurations of the CPI.

FIG. 8 illustrates representative scans and filtered spectra for these two configurations. For the upper curve, illustrated in FIG. 8a, the difference in frequency between chirp and anti-chirp may be 17±1 ps$^{-1}$ and for the lower curve it may be 49±1 ps$^{-1}$. From this difference in frequency one may expect the corresponding fringe spacings to be 110±7 μm and 39±1 μm, respectively. This corresponds well with the observed fringe spacings of 110±20 μm and 40±2 μm for the upper and lower scans, respectively. To further underline the analogy with the quantum effect, one can compare these values with the theoretically predicted values. For the limit of infinite chirp, the expected signal can be calculated by numerically integrating eq. 2, where $F_1$ and $F_2$ are the spectra of the chirped and anti-chirped pulses, respectively. That yields 99±5 μm and 37.4±0.7 μm in good agreement with the observed values. The scans in FIG. 8a may be recorded by varying the path delay in the autocorrelator in steps of 3 μm. The SFG signal may be detected within a bandwidth of 0.3 nm FWHM around 395.0 nm. The accuracy of both of these values may be limited by the resolution of a spectrometer (0.2 nm). The interference feature may be broader and have lower intensity in the second configuration because more bandwidth may be blocked.

Phase super-resolution is one of the most prominent examples of quantum metrology and can be achieved with number-path entangled states (or NOON states). In this technique a superposition may be generated in a typical two-path interferometer, one path of which incorporates a time delay. The required N-photon entangled state is a coherent superposition of either all N input photons taking path one or all N photons taking path two.

One way to realize the time-reversed version of a two-photon phase super-resolution is by adding a two-path interferometer in front of the autocorrelator. Alternatively, because type-II phase matching may be used, the polarization in one of the arms of the autocorrelator may be rotated from horizontal to vertical. This allows recombination of the beams from the two interferometer arms at a polarizing beam splitter (see FIG. 6d). Because the two beams have different polarizations a half-wave plate oriented at 22.5° may act like a beamsplitter on the two polarization modes. Specifically, it may create a superposition of the two beams with relative phase zero in the +45° polarization mode and a superposition with relative phase −1 in the −45° polarization mode. That means that the combination of half-wave plate and crystal may now effectively represent an autocorrelator with zero delay between its arms. The actual autocorrelator on the other hand can now be used as the first interferometer in the phase super-resolution analogue.

Figure 9:
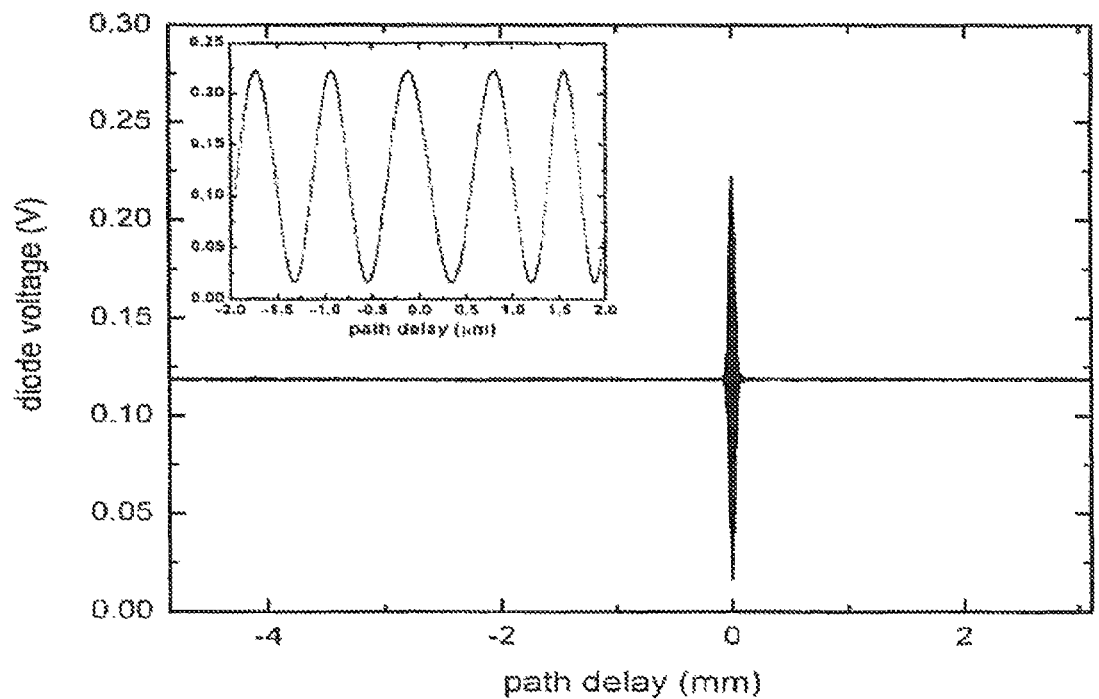
FIG. 9 illustrates the result of a continuous scan of SFG and white-light signal over the path delay in the autocorrelator.
Figure 9:
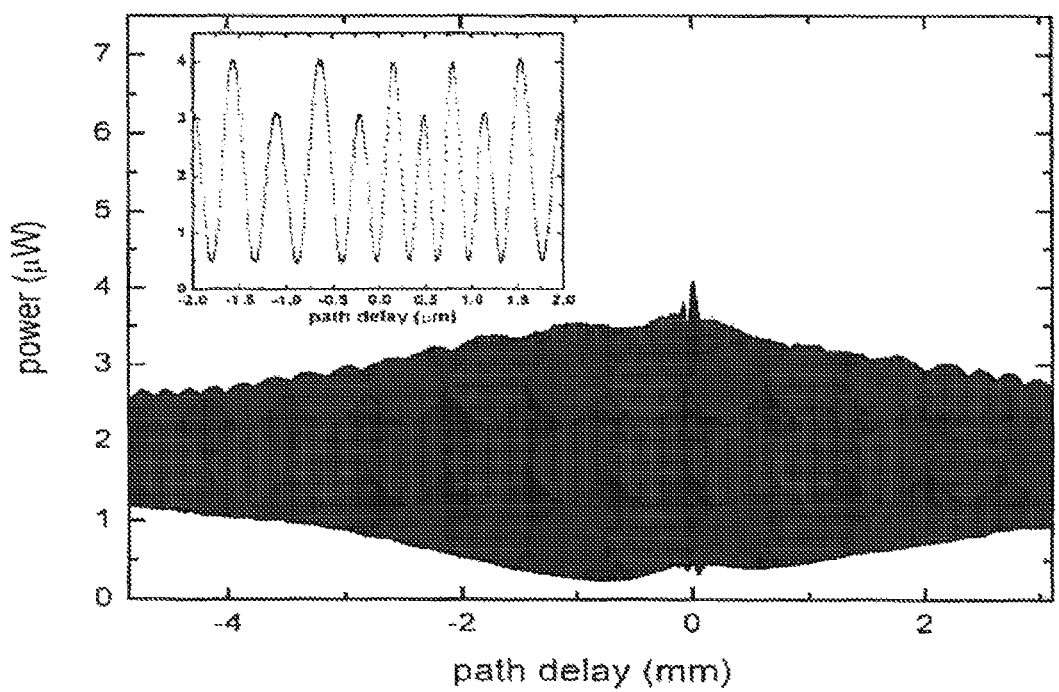

The lower panel illustrated in FIG. 9 shows the result of a continuous scan of the SFG signal over the path delay in the autocorrelator. For comparison the upper panel in FIG. 9 shows a white-light interferogram, wherein the half-wave plate is replaced with a polarizer at 45°, blocking the anti-chirped beam, and recording the fundamental signal (rather than the SFG) with a fast photo diode. The insets illustrated in FIG. 9 show that the phase super-resolution signal is modulated with twice the frequency of the modulation in the white-light interferogram. To be specific, white-light signal may have a fringe spacing of 795±8 nm, while the phase super-resolution signal may show a fringe spacing of 394.97±0.5 nm. The relatively large error in the white light interferometry (WLI) error may result from the fact that the WLI interferogram is much narrower. As a result it suffers noticeably more from the uncertainty of the velocity (~1%) with which the path delay is scanned. It should be noted that although the modulation wavelength in the phase super-resolution signal may be equal to the detected wavelength of the SFG signal, it may be the path delay of an infrared beam that is varied, yielding a modulation at twice the frequency. FIG. 9 shows a further characteristic of phase super-resolution. The width of the interferogram may not be limited by the coherence length of the pump pulses as it is for white-light interference.

As described, the CPI of the present invention may be used to implement three well-known two-photon interference effects: the Hong-Ou-Mandel peak, quantum beating and two-photon noon interference. The interferograms show the same characteristics as their quantum counterparts.

Aberration Cancellation

The present invention, in one aspect thereof, may be adapted to provide the advantages described above but with spatially, rather than temporally, chirped pulses.

The CPI, as described above, may use oppositely chirped laser pulses considering just two frequencies, $\omega_0+\Omega$ and $\omega_0-\Omega$ at a time. The signal may be constructed by the interference of these two frequencies (which should be insensitive to even-order temporal dispersion) and then summed over the course of the laser pulse. The signal may be generated via SFG and measured at a narrow bandwidth of the light near $2\omega_0$. To obtain the spatial aberration cancellation in 1-dimension, beams with oppositely correlated transverse wavevector $k_x=+\delta k$ and $k_x=-\delta k$ may be provided, where $k_x$ is the x-component of the wavevector (assuming that the light is primarily traveling along the z-direction so $\vec{k}=(k_x,0,\sqrt{K^2-k_x^2})$, $K=\omega/c$)). These beams may be coherently combined in a cross-correlator in which one arm contains a sample which can introduce spatial aberrations (along the x-direction). After interaction from the sample, both beams may be combined in a SFG material; one need only detect the SFG light with a transverse wavevector near 0.

Integration may be performed over different values of δk for example by a pair of tipping mirrors. This set of conditions may map the frequency-time degrees of freedom in CPI to transverse momentum/position degrees of freedom, the signal predicted to be insensitive to even-order aberrations in the x-direction. Cancellation of aberrations in both the x- and y-directions may require the input beams to have oppositely correlated wavevectors in both the x- and y-directions, but otherwise may typically work in the same way.

Physical constraints analogous to those described above may be encountered. In the above described aspect of the present invention, dispersion cancellation may work as long as the dispersion introduced by the sample is small relative to that used to create the chirp. In this spatial analogue, the aberrations should be small relative to the spatial chirp.

Additionally, it may be possible to combine spatial and temporal correlations, such as by using both momentum and frequency correlations to simultaneously cancel even orders of spatial and temporal dispersion.

Dispersion Cancelled Optical Coherence Tomography

As previously described, the HOM interferometer utilized in QOCT is based on entangled photon pairs and the costs, in terms of speed, and specialized & expensive equipment, have limited its widespread adoption. Other techniques for blind dispersion compensation without entanglement have been proposed or demonstrated, but they require unavailable technology or significant numerical post-processing and do not have the other properties of the HOM.

Based on time-reversal, the system of the present invention may be adapted to measure the axial profile of a sample accruing all of the benefits of the HOM over WLI. Similar to QOCT, the present invention, in one aspect thereof, introduces artifacts. However, the present invention, in one aspect thereof, provides a method for controlling these artifacts in such a way that would be technically difficult in QOCT.

In one aspect of the present invention, the CPI can be incorporated into an OCT system where a sample reflects light from one of the arms before being directed to the nonlinear crystal. For example, the CPI may be modified such that instead of reflecting from mirrors, in one arm a mirror is replaced by a sample, such as a microscope coverglass that provides two interfaces (the front and back surface) for the light to reflect from, giving a relatively straightforward sample that is not meant to limit the application of the present invention, but is provided for illustrative purposes only.

It can be demonstrated that, using a nontrivial sample, this adaptation provides a similar signal to the CPI signal derived above. In accordance with the above, it may be assumed that the effect of the sample is modelled by the transfer function, $H(\omega)$.

The reference arm of the adapted CPI may contain an adjustable path delay, $\Delta\tau$. After propagation in each arm, the beams may undergo SFG in a nonlinear medium, which may be detected in a very narrow frequency band near $2\omega_0$ ensuring that the output signal may be almost exclusively due to cross-correlations between the chirped and anti-chirped pulses. Under these conditions, signal measured by a square-law detector, $S(\Delta\tau)$, may be given by $$S(\Delta\tau) \propto \int d\Omega I(\Omega)I(-\Omega)|H(\Omega)|^2 - Re[\int d\Omega I(\Omega)I(-\Omega)H(\Omega) H^*(-\Omega)e^{-2i\Omega\Delta\tau}] \quad (6)$$

where $I(\Omega)$ is the intensity spectrum of each pulse and the integration over $\Omega$ is performed by the chirp. The signal may be identical to that in QOCT when $I(\Omega)I(-\Omega)$ is equal to the spectrum of the entangled photons.

Figure 10:
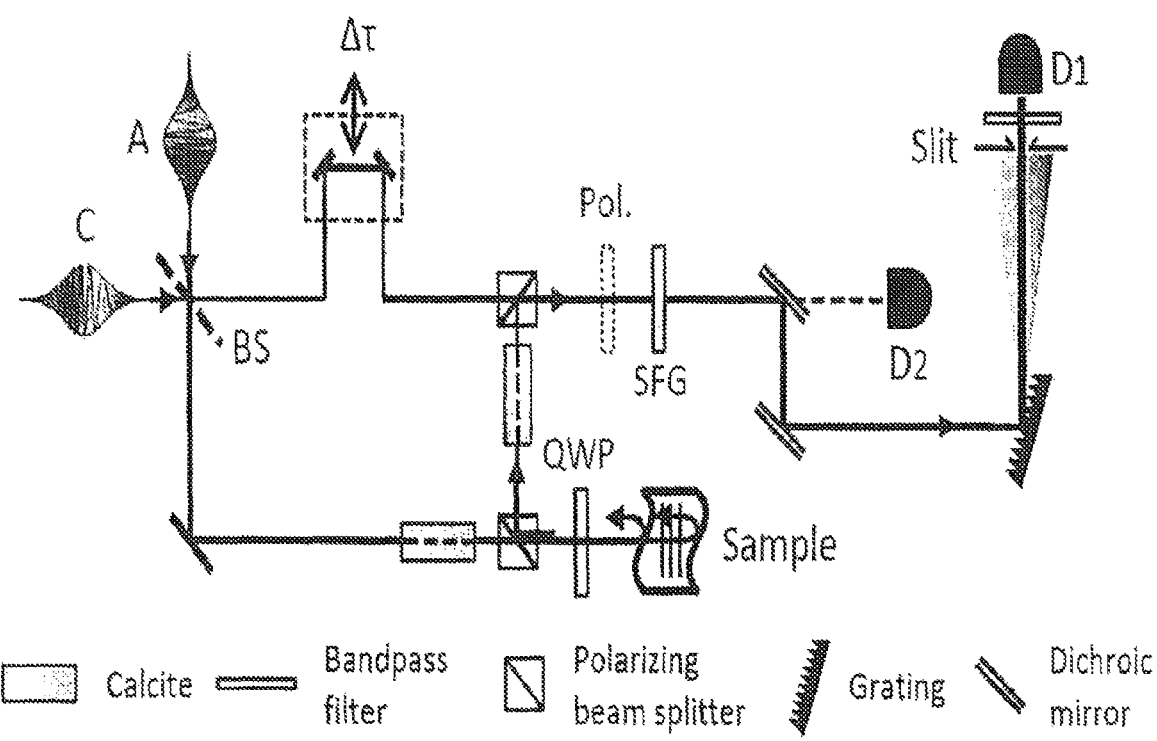
FIG. 10 illustrates the CPI adapted to QOCT in one aspect of the present invention.

FIG. 10 illustrates an example of an implementation in which the CPI is adapted to QOCT. The QOCT measurements may be shown using the example implementation described above with a borosilicate microscope coverglass as a sample. Light in the sample arm may pass through a polarizing beamsplitter (PBS) and quarter-wave plate (QWP). After reflection from the sample and a second pass through the QWP, the polarization may be vertical and the light may traverse the remainder of the sample path. The light in the reference arm may undergo a variable optical delay. The two beams may be recombined spatially, but with orthogonal polarizations, at the second PBS. This light may be focussed onto a 0.5 mm BBO crystal phase-matched for type-II SFG. Dichroic mirrors may separate the fundamental from the SFG light. A grating and slit may be used to filter a narrow band, 0.46 nm FWHM of SFG light before the light is detected by an amplified Si detector (D1). Alternatively, the fundamental light may be directly detected using a power meter (D2) by inputting only the chirped beam with a polarizer (Pol.) at 45 degrees before the nonlinear crystal. To see the effect of dispersion on the CPI and WLI, two calcite blocks could be inserted before and after the sample. The operating frequency may be measured either by taking a spectrum of the light after the first beamsplitter and measuring the wavelength at which the chirped and anti-chirped pulses interfere or by measuring the wavelength of the SFG near zero delay.

Figure 11:
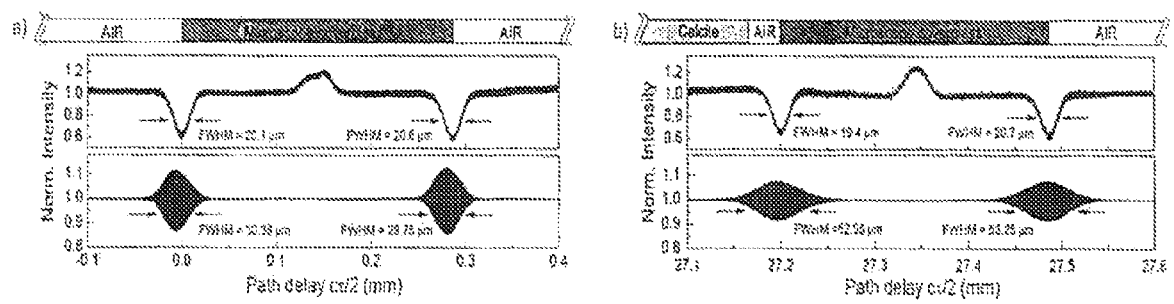
FIG. 11 illustrates data obtained without and with calcite blocks.

The chirped pulse interference and white light interference may be taken by continuously scanning the delay, $\Delta\tau$, and recording the detector (D1, D2) signal. FIG. 11 illustrates data obtained without (FIG. 11a) and with (FIG. 11b) calcite blocks, respectively, where the upper plot depicts chirped pulse interference and the lower plot depicts white light interference. As illustrated in FIG. 11a, without any additional calcite, the chirped pulse interference dips of the example implementation have widths 20.1±0.1 μm and 20.6±0.3 μm FWHM and corresponding visibilities of 39.0% and 40.9%. The white light interference patterns have widths 30.38±0.02 μm and 29.75±0.03 μm FWHM and corresponding visibilities of 12.9% and 14.0%. Even without the addition of the calcite, the chirped pulse interference signal has enhanced resolution by a factor of approximately 1.5.

Furthermore, by scanning the 0.5 mm range of delays and accumulating data over 0.5 s, a measured power level is observed that is 7 orders of magnitude higher than what could be achieved using QOCT using the best available technology.

The path delay between the two CPI interference dips in the example implementation is 286.15±0.02 μm. This can be converted to the physical thickness of the coverslip by dividing by the group index of borosilicate glass at operating wavelength (790.8±0.3)nm, $n_g$=1.53482. This yields an optical measurement of the coverglass thickness of 186.44±0.01 μm which is in good agreement with a direct measurement of the thickness using a micrometer of 186.4±0.8 μm.

The effects of material dispersion on the interference may be shown using a pair of calcite beam displacers inserted into the system. In an example implementation, the sum of their lengths may be 80.58±0.01 mm and the light may propagate with ordinary polarization. In this implementation, the widths of the CPI dips may be effectively unchanged at 19.40.5 μm and 20.7±0.2 μm FWHM while the WLI may be broadened by 74% to 52.95±0.06 μm and 53.25±0.04 μm. The somewhat larger uncertainty for the first CPI dip may be attributed to a sloped shoulder. Under these conditions, the CPI has a resolution 2.6 times that of WLI.

Both CPI and QOCT signals may contain artifacts. The origin of these features may be illustrated by measuring the full SFG spectrum as a function of delay using a high-resolution spectrometer. Cross-correlations may be detected whereas the autocorrelations may be broadband and too weak to be detected. When the paths are unbalanced, the signal may contain two doublets of narrow spectral lines. One of these pairs may be due to the chirped pulse traversing the sample arm and the anti-chirped pulse traversing the reference. The peaks may be separated in frequency because there may be a difference in optical delay between the component of the pulse reflected from the front surface versus the back surface. The sum of the instantaneous frequencies of the anti-chirped pulse and the chirped pulse reflected from the front surface may therefore be slightly higher in frequency than the sum of the antichirped pulse and the chirped pulse reflected from the back surface. The other doublet can be understood by swapping the roles of the chirped and anti-chirped pulses.

Changing the delay may change the spacing between the two doublets. When the optical delays between the reference path and the sample path are equal (for example, when the light reflecting from the front surfaces are equal), an interference dip may be observed due to the two different processes producing light at the same frequency but out of phase. From the geometry of the spectrum versus delay, one could see that there will be an additional pair of crossing points between the two real signals, which may give rise to the artifacts.

As in QOCT, the interference in these artifacts can be constructive or destructive. If constructive, the artifact may be a peak and may be easy to visually identify. If the interference is destructive, then artifacts could easily be confused with a real signal. In QOCT it was predicted that this could be adjusted by changing the sum-frequency of the entangled photon pair, however in practice this is difficult as most UV narrow-band pump sources for SPDC are not tuneable. The present invention, in one aspect thereof, has the advantage that the operating frequency is tuneable by simply changing the relative delay of the chirped and anti-chirped pulses at the input beamsplitter.

Figure 12:
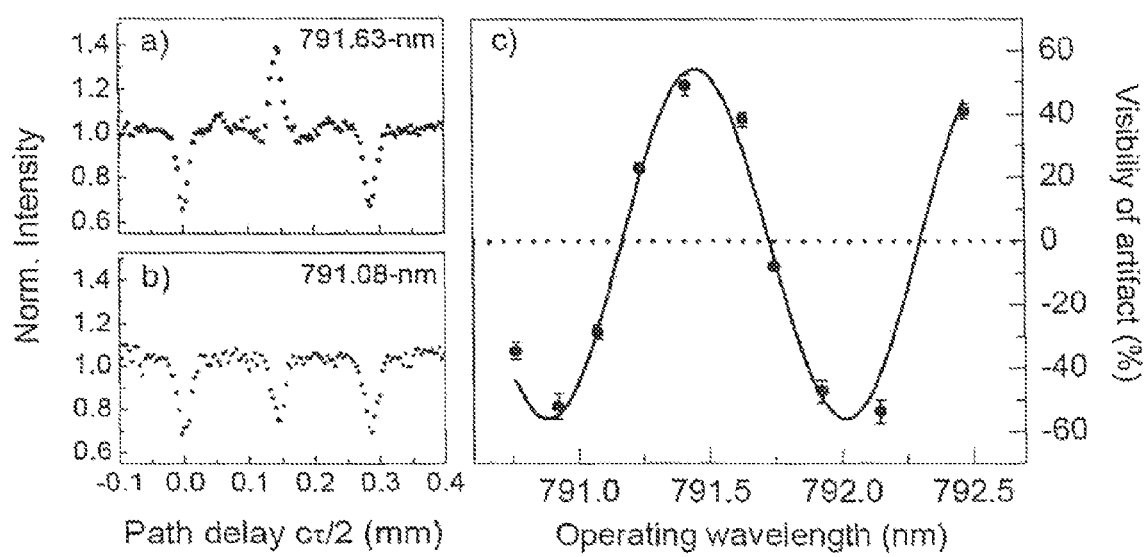
FIG. 12 illustrates two examples of interferograms generated by the system of the present invention, in one aspect thereof, taken at slightly different effective operating wavelengths 791.63 nm and 791.08 nm distinctly showing constructive and destructive interference in the artifact respectively.

FIG. 12 illustrates two examples of interferograms generated by the system of the present invention, in one aspect thereof, taken at slightly different effective operating wavelengths 791.63 nm and 791.08 nm distinctly showing constructive and destructive interference in the artifact respectively. The path delay corresponding to the illustrated interferograms is stepped instead of continuously varied.

Using the model transfer function for the coverslip, $H(\Omega) = r_1 + r_2 e^{i2k(\omega_0+\Omega)d}$, where $r_1$ ($r_2$) is the reflection amplitude from the front (back) surface, $k(\omega)$ is the wavevector in the glass, and d is the thickness. Inserting this expression into Eq. 6, it may be observed that the artifact term is modulated by cos $2k(\omega_0)$d. Making the approximation $k(\omega_0+\Omega) \approx k(\omega_0) + \alpha\Omega$, the expected change in wavelength required to flip the sign of the interference may be given as $\Delta\lambda \approx \lambda_0^2/(4n_g d)$, where $\lambda_0$ is the operating wavelength and $n_g = \alpha c$.

FIG. 12c illustrates the visibility of the artifact as a function of the operating wavelength. A fit to this data yields a period of (1.13±0.02) nm which is in good agreement with the theoretical prediction of 1.09 nm. This technique can be incorporated into a straightforward method for identifying, and subsequently removing artifacts from axial scans.

As described above, the present invention may be operable to provide the benefits of QOCT using the CPI, but with dramatic increases in signal, direct optical detection, and a straightforward means of identifying artifacts. The CPI implementation adapted for QOCT achieves the benefits of quantum interferometry at macroscopic power levels and represents a powerful new technique for optical imaging. More generally, this work clarifies the role of entanglement versus correlation in quantum imaging.

Artifact-Free Dispersion Cancelled Optical Coherence Tomography

Further modifications may be made to the CPI to enable yet further advantages over the prior art. The modifications include switching from bulk optics stretchers and from compressors to using other pulse shaping techniques than those described above; a method of eliminating artifacts from the signal (rather than merely identifying them); and reducing the power sent through the sample.

In one aspect of the present invention, by switching from bulk optics stretchers and compressors to pulse shaping, the system of the present invention may retain its operability while retaining more power and allowing more flexibility over implementation parameters. Additionally, the system may be implemented at a cheaper cost by replacing a computer controlled shaper with a single custom designed optical element.

As previously described, the frequencies of the interference giving rise to artifacts may be different than those giving rise to the real signals. In one aspect of the present invention, the artifacts may be completely ignored by providing stringent spectral filtering, which may also provide an implementation wherein the CPI is inherently background free. Although the CPI as described above may comprise destructive interference (meaning that narrowly filtering the signal may result in loss of interference data), by switching to the constructive interference described above, the CPI may be operable to achieve background free, artifact free, dispersion-cancelled images.

In another aspect of the present invention, to reduce the power sent through the sample, the reflectivity of the beamsplitter may be altered such that only a small fraction of the power passes through the sample; the rest may be routed through the reference arm. In the single beam configuration possible with the constructive interference, this may be relatively easy to implement.

By combining the implementations described above, wherein one of the mirrors in the cross-correlator is replaced with a sample, such as a microscope slide as the simplest sample, with multiple interfaces and wherein the operating frequency of the chirped pulses is changed, the present invention, in one aspect thereof, provides an imaging system without artifacts and with reduced background noise. In addition, a pulse shaping device may be provided rather than laser beams in order to eliminate further undesirable characteristics mentioned previously.

The device may be computer controlled and write an arbitrary phase and amplitude pattern as a function of frequency. This may provide flexibility for the degree of chirp and remove any phase fluctuations.

Figure 14:
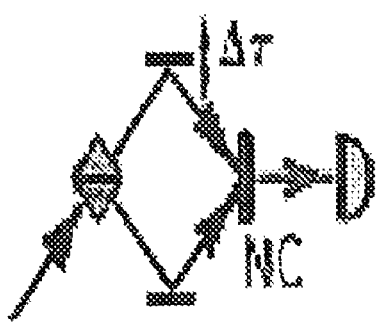
FIG. 14 illustrates the use of a pure dispersive phase shift enabling the CPI of the present invention, in one aspect thereof, to be operable with one input optical beam.

Furthermore, instead of creating frequency anticorrelations through superposition of two pulses, such as chirped and antichirped pulses, a pure dispersive phase shift may be utilized, wherein the pure dispersive phase shift is applied to a single beam. FIG. 14 illustrates the use of a pure dispersive phase shift enabling the CPI of the present invention, in one aspect thereof, to be operable with one input optical beam.

For example, the shift may be given by $$\phi(\omega) = A(\omega-\omega_0)^2, \text{ if } \omega > \omega_0 \text{ and } \phi(\omega) = -A(\omega-\omega_0)^2, \text{ if } \omega < \omega_0.$$

The time delay may correspond to a derivative of this phase with respect to frequency and thus may correspond to $\tau\alpha|\omega-\omega_0|$. Pairs of anticorrelated frequencies may be delayed by the same time and the time-frequency correlations required for chirped-pulse interferometry may be created. Artifacts may be inherent in quantum optical coherence tomography and in the classical analogue demonstrated by the present invention. These artifacts may be identified since they are phase sensitive, while the real signals may not be.

Figure 13:
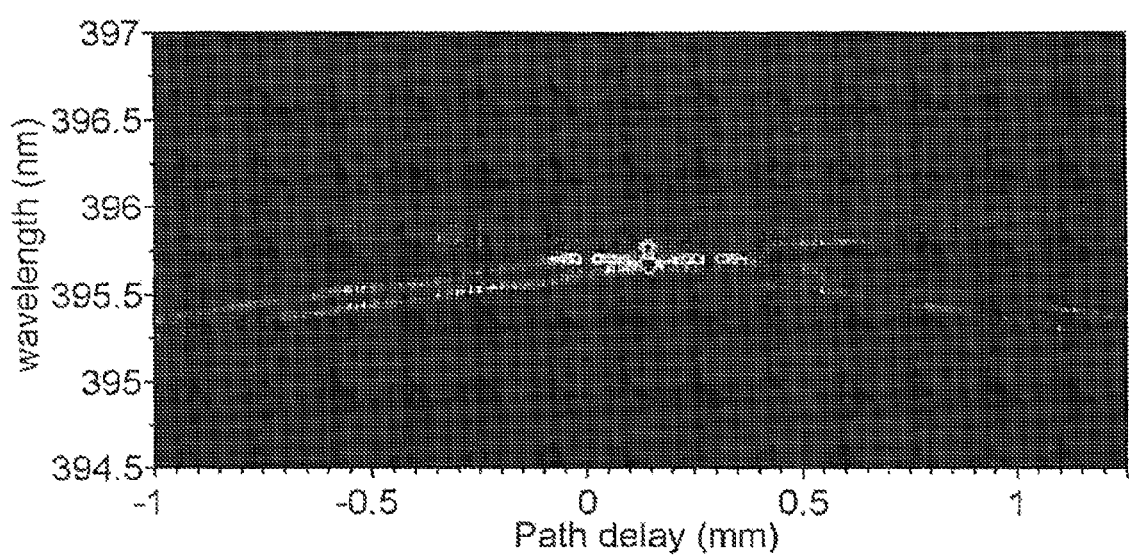
FIG. 13 illustrates the interference dips corresponding to the front and back surface occurring at frequencies corresponding to twice the operating frequency.

A novel method may be provided for eliminating the artifacts. FIG. 13 illustrates the interference dips corresponding to the front and back surface occurring at frequencies corresponding to twice the operating frequency (i.e. along the symmetry axis of the spectrum). One can also see that the artifacts necessarily occur at different frequencies. By narrow spectral filtering, the artifacts can be effectively ignored in the final signal.

However, if one filters too narrowly the dispersion cancellation may be completely lost. One may need to optimize the filtering level so as to remove the artifacts without losing dispersion cancellation. By using a single beam of correlated frequencies, as described above, constructive interference may be produced.

Finally, to reduce the power level passing through the sample, an unequal beamsplitter may be used as the first beamsplitter to the cross-correlator to direct only a small amount of light through the sample and direct most of the power around the sample (i.e. the reference). The chirped-pulse signal shape (not level) may be loss insensitive and this method could be used to reduce the flux through the sample at a modest cost of signal level. Combining these techniques may provide for axial imaging of samples with relatively low power, no artifacts, and high signal to noise ratio. The pulse shaper may remove phase fluctuations in the output signal and allow for one to tradeoff the output power (which increases with less chirp) with the level of dispersion cancellation (which increases with more chirp). These improvements may provide for axial imaging of complex biological samples with the advantages originally promised in QOCT.

Other

Further applications of the present invention, and adaptations thereof, may be provided as could be appreciated by a person skilled in the art. These may include but are not limited to: a novel method for measuring $3^{rd}$-order dispersion; measuring group velocity dispersion; characterizing the group delays or group velocities in materials including free space, photonic devices, biomedical tissue, fibre optics; and reproducing other quantum interference phenomena, including quantum beating.

The invention claimed is:
1. An interferometer system for measuring optical properties of a sample, the interferometer system characterised by:
 (a) a light source apparatus operable to emit at least one shaped laser pulse toward a beam splitting apparatus;
 (b) the beam splitting apparatus operable to (i) mix the at least one shaped laser pulses so as to define a mixed beam; and (ii) separate the mixed beam so as to define two resulting beams, a first resulting beam directed to a reference arm and a second resulting beam directed to a sample arm, the sample being associated with the sample arm;
 (c) a combining apparatus operable to receive the two resulting beams after the two resulting beams exit the reference arm and the sample arm, the combining apparatus combining, using a means of optical nonlinear mixing, the two resulting beams into a product beam, the combining apparatus further directing the product beam towards a detection point; and
 (d) a detector operable to record at the detection point an interference pattern for defining the optical properties, the interference pattern corresponding to the product beam.

2. The system as claimed in claim 1, further characterised by a directing apparatus disposed between the beam splitting apparatus and the combining apparatus, the directing apparatus operable to direct at least one of the resulting beams such that the two resulting beams after exiting the reference arm and the sample arm are directed towards a meeting point.

3. The system as claimed in claim 2, characterised in that the directing apparatus is one or more mirrors.

4. The system as claimed in claim 1, characterised in that two shaped laser pulses are provided, wherein the two shaped laser pulses have time correlations between anticorrelated frequencies.

5. The system as claimed in claim 4, characterised in that the two shaped pulses are oppositely chirped.

6. The system as claimed in claim 5, characterised in that the two shaped laser pulses are emitted by two different synchronized lasers, one producing a chirped pulse and the other producing an antichirped laser pulse.

7. The system as claimed in claim 5, characterised in that the system's resolution is increased by increasing the bandwidth of the chirped pulses.

8. The system as claimed in claim 4, characterised in that the frequency difference between the two shaped pulses is swept to determine the centre of a dip in the interference pattern.

9. The system as claimed in claim 4, characterised in that the operating frequency of the system is tuneable by changing the relative delay between the shaped laser pulses at the beam splitting apparatus.

10. The system as claimed in claim 4, characterised in that the light source apparatus includes a means of blocking part of the spectrum of one of the two shaped laser pulses for producing quantum beating in the interference pattern.

11. The system as claimed in claim 1, characterised in that the light source apparatus is a modelocked laser.

12. The system as claimed in claim 11, characterised in that the modelocked laser is a ti:sapphire laser.

13. The system as claimed in claim 1, characterised in that the beam splitting apparatus is a beamsplitter.

14. The system as claimed in claim 13, characterised in that the beamsplitter is a 50/50 beamsplitter.

15. The system as claimed in claim 1, characterised in that the beam splitting apparatus is an acousto-optic modulator.

16. The system as claimed in claim 1, characterised in that the combining apparatus is a non-linear material and the product beam is a sum-frequency generation of the resulting beams.

17. The system as claimed in claim 16, characterised in that the non-linear material is a crystal.

18. The system as claimed in claim 1, characterised in that the means of optical nonlinear mixing automatically compensates for dispersion between the two resulting beams.

19. The system as claimed in claim 1, characterised in that adjusting the length of the reference arm changes the relative timing of the resulting beams.

20. The system as claimed in claim 1, further characterised by a filter placed between the combining apparatus and the detection point, the filter having a bandwidth narrower than the bandwidth of the shaped laser pulses, such that the interference pattern has a visibility of up to 100%.

21. The system as claimed in claim 1, further characterised by a filter placed between the combining apparatus and the detection point, the filter operable to remove frequencies corresponding to an autocorrelation background of the interference pattern, such that the interference pattern has a visibility of up to 100%.

22. The system as claimed in claim 1, characterised in that the means of optical nonlinear mixing provides the interference pattern with a visibility that is insensitive to unbalanced loss.

23. The system as claimed in claim 1, characterised in that the laser pulses are spatially correlated to cancel aberration in the interference pattern.

24. The system as claimed in claim 1, characterised in that one shaped laser pulse is provided, wherein the one shaped laser pulse is a pure dispersive phase shifted laser pulse.

25. The system as claimed in claim 1, characterised in that the system further comprises a beam overlapping apparatus between the light source apparatus and the beam spilitting apparatus for producing a Hong-Ou-Mandel peak in the interference pattern.

26. The system as claimed in claim 1, characterised in that the beam splitting apparatus is further operable to rotate the polarization of one of the two resulting beams for producing phase super-resolution in the interference pattern.

27. An interferometric method for measuring optical properties of a sample, the interferometric method characterised by:
 (a) generating at least one shaped laser pulse;
 (b) mixing the at least one shaped laser pulse so as to define a mixed beam;
 (c) separating the mixed beam so as to define two resulting beams, a first resulting beam directed to a reference path and a second resulting beam directed to a sample path, the sample associated with the sample path; and
 (d) combining, by optical nonlinear mixing, the two resulting beams after the two resulting beams exit the reference path and the sample path into a product beam, the product beam corresponding to an interference pattern for defining the optical properties.

28. The method as claimed in claim 27, characterised in that two shaped laser pulses are provided, wherein the two shaped laser pulses have time correlations between anticorrelated frequencies.

29. The method as claimed in claim 28, characterised in that the two shaped pulses are oppositely chirped.

30. The method as claimed in claim 29, characterised in that the two shaped laser pulses are emitted by two different synchronized lasers, one producing a chirped pulse and the other producing an antichirped laser pulse.

31. The method as claimed in claim 29, characterised in that the resolution of the measurement is increased by increasing the bandwidth of the chirped pulses.

32. The method as claimed in claim 28, characterised in that the frequency difference between the two shaped pulses is swept to determine the centre of a dip in the interference pattern.

33. The method as claimed in claim 28, characterised in that the two shaped laser pulses are overlapped prior to mixing for producing a Hong-Ou-Mandel peak in the interference pattern.

34. The method as claimed in claim 28, characterised in that part of the spectrum of one of the two shaped laser pulses is blocked for producing quantum beating in the interference pattern.

35. The method as claimed in claim 27, characterised in that the two shaped laser pulses are emitted by a modelocked laser.

36. The method as claimed in claim 35, characterised in that the modelocked laser is a ti:sapphire laser.

37. The method as claimed in claim 27, characterised in that a beamsplitter mixes the two shaped laser pulses and separates the mixed beam.

38. The method as claimed in claim 37, characterised in that the beamsplitter is a 50/50 beamsplitter.

39. The method as claimed in claim 37, characterised in that the beamsplitter is an acousto-optic modulator.

40. The method as claimed in claim 27, characterised in that a non-linear material combines the two resulting beams and the product beam is a sum-frequency generation of the resulting beams.

41. The method as claimed in claim 40, characterised in that the non-linear material is a crystal.

42. The method as claimed in claim 27, characterised in that the optical nonlinear mixing automatically compensates for dispersion between the two resulting beams.

43. The method as claimed in claim 27, characterised in that adjusting the length of the reference path changes the relative timing of the resulting beams.

44. The method as claimed in claim 27, further characterised by filtering the product beam using a filter having a bandwidth narrower than the bandwidth of the shaped laser pulses, such that the interference pattern has a visibility of up to 100%.

45. The method as claimed in claim 27, further characterised by filtering the product beam using a filter operable to remove frequencies corresponding to an autocorrelation background of the interference pattern, such that the interference pattern has a visibility of up to 100%.

46. The method as claimed in claim 27, characterised in that the optical nonlinear mixing provides the interference pattern with a visibility that is insensitive to unbalanced loss.

47. The method as claimed in claim 27, characterised in that the laser pulses are spatially correlated to cancel aberration in the interference pattern.

48. The method as claimed in claim 27, characterised in that one shaped laser pulse is provided, wherein the one shaped laser pulse is a pure dispersive phase shifted laser pulse.

49. The method as claimed in claim 27, characterised in that polarization of one of the two resulting beams is rotated for producing phase super-resolution in the interference pattern.

* * * * *